United States Patent
Huiku (10) Patent No.: US 7,407,485 B2
(45) Date of Patent: Aug. 5, 2008

(54) MONITORING PAIN-RELATED RESPONSES OF A PATIENT

(75) Inventor: Matti Huiku, Espoo (FI)

(73) Assignee: Instrumentarium Corporation, Helsinki (FI)

( * ) Notice: Subject to any disclaimer, the term of this patent is extended or adjusted under 35 U.S.C. 154(b) by 969 days.

(21) Appl. No.: 10/863,719

(22) Filed: Jun. 8, 2004

(65) Prior Publication Data

US 2005/0272984 A1   Dec. 8, 2005

(51) Int. Cl.
*A61B 5/00* (2006.01)
*A61B 5/05* (2006.01)

(52) U.S. Cl. .................. 600/300; 600/485; 600/544; 600/546; 600/547

(58) Field of Classification Search ............ None
See application file for complete search history.

(56) References Cited

U.S. PATENT DOCUMENTS

| | | | |
|---|---|---|---|
| 4,570,640 A | 2/1986 | Barsa | |
| 6,120,443 A * | 9/2000 | Cohen-Laroque | 600/300 |
| 6,571,124 B1 | 5/2003 | Storm | |
| 6,622,035 B1 | 5/2003 | Storm | |
| 6,654,632 B2 * | 11/2003 | Lange et al. | 600/544 |
| 6,990,372 B2 * | 1/2006 | Perron et al. | 600/544 |
| 2002/0138018 A1 * | 9/2002 | Lange et al. | 600/544 |
| 2002/0183605 A1 | 12/2002 | Devlin et al. | |
| 2007/0010723 A1 * | 1/2007 | Uutela et al. | 600/301 |

FOREIGN PATENT DOCUMENTS

| | | |
|---|---|---|
| EP | 0 553 162 | 5/1997 |
| EP | 1 273 265 | 1/2003 |
| WO | WO-02/32305 | 4/2002 |
| WO | WO-02/100267 | 12/2002 |
| WO | WO-03/086188 | 10/2003 |
| WO | WO-03/094726 | 11/2003 |

OTHER PUBLICATIONS

*Automatic Detection of Nausea Using Bio-Signals During Immerging in a Virtual Reality Environment*, Y. H. Nam et al., 2001 Proceedings of the 23rd Annual EMBS International Conference, Oct. 25-28, Istanbul, Turkey, pp. 2013-2015.
*Skin conductance correlates with perioperative stress*, H. Storm et al., Acta Anaesthesiol. Scand. 2002, 46: 887-895.
*Clinical implementation of advanced control in anesthesia*, D. A. Linkens et al., Transactions of the Institute of Measurement and Control 22,4 (2000), pp. 303-330.

* cited by examiner

*Primary Examiner*—Robert L Nasser
(74) *Attorney, Agent, or Firm*—Andrus, Sceales, Starke & Sawall, LLP (57) ABSTRACT

The invention relates to monitoring of pain-related responses in a patient in order to detect the level of pain experienced by the patient. At least one first measurement signal is acquired from the patient and at least one of the signals is transformed into a normalized signal having a predetermined value range. Based on the at least one normalized signal obtained in this way, a threshold condition is set and a rate at which at least one second measurement signal fulfills the threshold condition is monitored, wherein each of the at least one second measurement signal is derivable from a corresponding normalized signal and indicative of pain-related activity in the patient. The level of pain experienced by the patient depends on the rate monitored.

43 Claims, 6 Drawing Sheets

Group Average

FIG. 4b

Individual Patient Distribution

Parameter Value

FIG. 4c

Partially Adapted Patient Distribution

FIG. 4d

Cumulative Patient Distribution

Parameter Value

MONITORING PAIN-RELATED RESPONSES OF A PATIENT

FIELD OF THE INVENTION

The present invention relates generally to a method and apparatus for monitoring pain-related responses in a patient. In this context, pain-related responses refer mainly to noxious responses, which are reactions that may be detected in the patient in response to noxious stimuli and which the patient may sense as pain. However, pain-related responses may also be non-noxious responses which are indicative of absence of pain.

BACKGROUND OF THE INVENTION

Pain is an unpleasant sensory or emotional experience that is associated with actual or potential tissue damaging stimuli. It is always an individual and subjective sensation, which may be acute (nociceptive), elicited by noxious stimuli, or chronic pain that has outlived its usefulness to preserve tissue integrity. The perception of pain takes mainly place at cortex, and it may be suppressed in deep sedation and anesthesia by the general (global) inhibitory effects of sedative drugs and anesthetic agents. The responses to noxious stimulus may also be suppressed when the pain signal pathway is sufficiently suppressed at the subcortical level, often in the region of the brainstem and spinal cord. Both cortical and subcortical mechanisms play a role in pain management in modern surgical anesthesia or intensive care.

Analgesia refers to the absence of pain or loss of sensitivity to pain without unconsciousness in response to stimulation that would normally be painful.

Noxious stimuli, such as pin pricks or inflammation exceeding a certain threshold stimulus level in nociceptive nerve fibers (nociceptors), cause a nociception, i.e. a neuronal signal or perception that denotes the induced pain or injury. Nociception is transmitted in the Central Nervous System (CNS) via several different ascending pathways causing responses that can be cortical pain responses or subcortical stress responses. NSAIDs (Non-Steroidal Anti-inflammatory Drugs) effectively relief pain at a damaged tissue site, whereas opioids selectively affect the pain pathways in the region of the spinal cord or the brainstem. The local anesthetic agents, for instance those used in epidural analgesia, block both the pain and the sensory pathways in the spinal cord region.

Antinociception normally refers to the blocking or suppression of nociception in the pain pathways at the subcortical level. It may be described as subcortical analgesia, in distinction to preventing the perception of pain at the cortex, i.e. cortical analgesia.

Sedation is a drug-induced state of a patient, during which the patient may respond normally to verbal commands or tactile stimulation and is not agitated or anxious (mild sedation), or during which the patient responds only to loud commands or tactile stimulation (moderate or conscious sedation), or during which the patient is unconscious and not easily arousable, but responds only to repeated or painful stimulation (deep or unconscious sedation). Anesthesia, in turn, is the deepest drug-induced state of sedation, during which the patient is not arousable, even by painful stimulation.

Agitation is often defined as the motor restlessness that accompanies anxiety. Mild or moderate sedation is induced to remove the agitation and to ensure optimal patient management. Optimal level of sedation varies with the stimulation affecting the patient and is often achieved, for ventilated patients, at the deepest sedation, accompanied with sufficient analgesia.

The autonomic nervous system (ANS) is the 'unconscious' nervous system, which controls and regulates virtually all of our basic body functions, such as cardiac function, blood circulation and glandular secretion. The main parts of the ANS are the parasympathetical and sympathetical nervous branches. The sympathetical nervous system usually prepares us for high stress situations by speeding up the body functions. Under conditions of normal ANS regulation, the parasympathetical system restores the normal conditions in blood circulation by slowing down the heart rate. Pain, discomfort, and surgical stress may activate the sympathetical branch of the ANS and cause an increase in blood pressure, heart rate and adrenal secretions.

Neuromonitoring is a subfield of clinical patient monitoring focused on measuring various aspects of brain function and on changes therein caused by drugs commonly used to induce and maintain anesthesia in an operation room or sedation in patients under critical or intensive care.

Electroencephalography (EEG) is a well-established method for assessing brain activity by recording and analyzing the weak biopotential signals generated in the cortex of the brain with electrodes attached on the skin of the skull surface. The EEG has been in wide use for decades in basic research of the neural systems of the brain, as well as in clinical diagnosis of various neurophysiological diseases and disorders.

Electromyography (EMG) is a method for recording electrical biopotentials of muscles. In an EMG measurement, the electrodes are attached on the surface of the skin at a muscle group. An EMG signal is often recorded from the skull of the patient, whereby the recorded signal indicates both the activity of the facial muscle (fEMG) and the brain (EEG). As the frequencies of the EMG spectrum are usually high and above the frequencies of brain activity, the signal components can be separated by methods of signal processing or spectral analysis from the EEG signal.

Electrocardiography (ECG) is another well-established method for assessing cardiac function by recording and analyzing the biopotential signals generated in the heart. Electrodes are attached on the skin of the chest with more peripheral references. The ECG is commonly used for diagnosing cardiac dysfunctions, various cardiac and circulatory diseases, and arrhythmias. Heart rate (HR), often derived from the ECG waveform, is one of the most important parameters characterizing the condition of a patient.

Respiration rate is another vital sign, which is often monitored even in basic patient care. In connection with anesthesia and sedation of ventilated patients, monitoring of the respiration is often combined with monitoring of gas exchange, which includes monitoring of inhaled and exhaled oxygen, carbon dioxide and anesthetic gases. In modern gas monitors, airway pressure (AWP) and gas flows are also measured in order to improve the safety and quality of the ventilation.

Blood pressure (maintaining blood circulation) is yet another vital sign obtained from a patient. It may be monitored either non-invasively (NIBP) or invasively (InvBP) using catheters inserted in the arteries or veins. The latter techniques are continuous and they allow a detailed monitoring of the regulation of the cardiac-circulatory and pulmonary functions.

Pulse oximetry is a well-established technique for measuring oxygen saturation (SpO2) in arterial blood. SpO2 is an important parameter, nowadays often called as the fourth vital sign, which relates to the adequacy of oxygen supply to peripheral tissues and organs. Pulse oximeters also display a photoplethysmographic (PPG) pulse waveform, which can be related to tissue blood volume and blood flow, i.e. the blood circulation, at the site of the measurement, typically in finger or ear. The amplitude of a PPG waveform is a sensitive indicator of patient discomfort and pain, but it also reacts to non-noxious stimulations.

Analysis methods using the heart rate variability (HRV) are emerging techniques for diagnosing cardiac diseases, such as lack of oxygen supply to the cardiac muscle, and for characterizing the cardiac function and the condition of the patient in general. Fast changes in the heart rate are usually caused by the parasympathetical ANS control mediated in the vagal cranial nerve. Vagal control slows down the heart beat. The slow variations (<0.15 Hz) of the heart rate are mainly associated with sympathetical activity, which accelerates the heart beat. The ratio of the fast components of the HRV to the slow components of the HRV is often called the sympatho-vagal balance, which in emergency or during intense surgical stress turns to sympathetical dominance.

One of the special applications to which a significant amount of attention has been devoted during the past few years is the use of processed EEG signals for objective quantification of the brain function for the purpose of determining the level of consciousness. Here, the basic idea is to automatically detect if the subject or patient is asleep or awake. Specifically, this has become an issue, both scientifically and commercially, in the context of measuring the depth of anesthesia during surgery. The concept of the adequacy of anesthesia, which is a broader concept, further includes various other aspects relating to the quality of anesthesia, such as the state of the autonomic nervous system (ANS), and more specifically analgesia, i.e. loss of sensation of pain.

The assessment, measurement, or control of the different components of anesthesia or sedation is difficult and sometimes poorly defined, as the drugs used are often unspecific and influence many components simultaneously. The cortical components, i.e. hypnosis, amnesia (loss of memory) and perception of pain and conscious control of movements, mainly refer to the activity of the cortex and integrity of the cortical evaluations of the sensory afferent inputs and the ability to store information and control the body. Loss of consciousness, i.e. loosing responses to non-noxious sensory stimulations, such as spoken commands, is dominantly related to the overall suppression of cortical processing and awareness, which already in an early phase of light sedation lead to the loss of explicit memory. Therefore, the monitoring of the loss of consciousness and/or awareness is usually enough to guarantee an adequate amnesia of the patient, as well.

During the past few years, several commercial devices for measuring the level of consciousness and/or awareness in a clinical set-up during anesthesia have become available. These devices, which are based on a processed one-channel EEG signal, have been introduced by Aspect Medical (Bispectral Index), by Datex-Ohmeda (Entropy Index) and by Danmeter (an auditory evoked EEG potential monitoring device, AAI™). At present, the situation with the assessment of the cortical activity and integrity is considered satisfactory, though not resolved for all applications.

As to the central nervous system (CNS), the assessment or measurement of the suppression of the sub-cortical activity, the ANS and the integrity of subcortical evaluations is far more unsatisfactory. No commercial devices exist for this purpose. This is mainly because the sub-cortical components are not represented in any single bioelectrical or other signal, in contrast to that the EEG almost alone may represent the cortical activity. The monitoring of the adequacy of anesthesia or sedation thus—in addition to monitoring the hypnotic state of brains by EEG—call for a multi-parameter approach, which combine parameters describing the overall responsiveness of the patient to "unconscious" stimulations. This may be defined by means of the hemodynamic, motor, and endocrine stability. A promising basis for searching a multi-parameter monitoring method for sub-cortical activity can thus possibly be found from the subtle features in the common vital signs, the heart rate, the respiration rate, the blood circulation, and the blood pressure.

The sub-cortical integrity of the afferent input, ANS evaluations, and efferent output is best researched with noxious stimulations and their responses, as these are mainly processed and modulated in the brainstem and spinal levels. The responses can also be modulated (attenuated) by analgesic or antinociceptive drugs, which influence the pain pathways at the sub-cortical levels. A successive monitoring method shall thus demonstrate a clear relationship and correlation between both the effect (concentration) of the analgesics on the suppression of the nociceptive responses and the intensity of the noxious stimulations on the strength or amount of the responses in the parameters.

The need for reliable monitoring of the adequacy of anesthesia is based on the quality of patient care and on economy related aspects. Balanced anesthesia reduces surgical stress and there is firm evidence that adequate analgesia decreases postoperative morbidity. Awareness during surgery with insufficient analgesia may lead to a post-traumatic stress disorder. Prolonged surgical stress sensitizes the central pain pathways, which post-operatively increases patient pain and secretion of stress hormones. Low quality pre- and intra-operative analgesia makes it difficult to select the optimal pain management strategy later on. More specifically, it may cause exposure to unwanted side effects during the recovery from the surgery. Too light an anesthesia with insufficient hypnosis causes traumatic experiences both for the patient and for the anesthesia personnel. From economical point of view, too deep an anesthesia may cause increased perioperative costs through extra use of drugs and time, and also extended time required for post-operative care. Too deep a sedation may also cause complications and prolong the usage time of expensive facilities, such as the intensive care theater.

International patent application WO 02/32305 discloses a method and device for ascertaining the cerebral state of a patient. In this disclosure, a measure derived from EMG signal data enhances and confirms the determination of the hypnotic state made using EEG signal data. As the EMG data may be computed more frequently than the EEG data, this renders ascertaining changes in the hypnotic state of the patient more rapid. In this method, the (facial) EMG thus alone reflects the suppression of the nociceptive pathways. State entropy (SE), which is calculated in the low frequency band up to 32 Hz, is dominated by the cortical EEG activity, while response entropy (RE), which also includes the high frequencies, represents both the cortical and muscle activity. The difference RE-SE is, therefore, a measure of the (f)EMG power, which will increase at nociception and which, therefore, may be a good measure of the suppression of the pain pathways. However, the above-mentioned dependency on the medication of the patient may render the method unusable in certain situations. As the (facial) electromyography signal is affected by neuro-muscular blocking agents (NMBAs), which suppress signaling at the nerve-muscle junctions, the EMG component of the measurement may vanish and render the method unusable, if the medication of the patient includes neuro-muscular blocking agents. It shall also be emphasized that the difference RE-SE is not specific to the suppression of the pain pathways but also reflects the overall motoric activity following any arousals—that is emotional or normal sensory evoked arousals, too. For instance, when the patient is awake and not perceiving any pain or discomfort, the RE-SE difference is typically about 8-10 percent. At deep hypnosis it is obvious that only painful stimulations can cause RE to differ from SE, but it is difficult to tell at which level the transition to the only-nociception induced varying difference in the deep anesthetia takes place.

EP patent 0553162 proposes a method and apparatus for assessing the depth of anesthesia by using respiratory sinus arrhythmia (RSA) as a measure of the state of the brain. The document describes a method in which a parameter indicative of clustering of the heart beat pattern is determined from the ECG waveform relative to the beginning of each respiration cycle. This parameter is then compared with a reference value calculated using a test for randomness. The parameter is then compared with the reference value to derive a measurement of the depth of anesthesia. In particular with spontaneously breathing anesthetized patients, the clustering is proportional to the RSA, which decreases with deepening anesthesia. The heart rate changes influencing the clustering are primarily controlled by the parasympathetical branch of the ANS, and therefore, the depth of anesthesia is related to the parasympathetical activity. This, however, correlates poorly with sympathetical effects, i.e. with the pain and nociception, and therefore also poorly with the adequacy of analgesia. Furthermore, the clustering takes place differently in artificial overpressure ventilation and in spontaneously breathing patients, as the heart rate always accelerates during the low pressure period of the respiration cycle and decelerates during the high pressure phase. The low pressure period occurs during the inspiration in case of spontaneously breathing patients and during the expiration in case of artificial ventilation. The proposed method works reasonably well for spontaneously breathing patients, who in addition have a large RSA, such as children, but often fails in connection with artificially ventilated older patients. Pain reduces RSA amplitudes, as does the deepening of anesthesia. As a result, a low value of clustering may suggest too deep an anesthesia, leading to a decrease in the level of hypnosis. This may, however, lead to a worse situation, as a result of which the patient may even wake up, especially if surgical stimulations are intense.

U.S. Pat. No. 6,120,443 also suggests a method based on a heart beat interval (ECG R-to-R peak interval, RRI) analysis to assess the depth of anesthesia. In this method, the degree of randomness of the heart beats is described by means of a fractal dimension of the series of the R-R Intervals, mathematically describing the correlation within the RRI series. High correlation is indicative of a low fractal dimension and of only very few (CNS) processes, which add irregularities in the RRI series. Low correlation and thus high randomness equals high fractal dimension, which implies that the anesthesia is light and that many processes influence the RRI series. The methods for calculating the fractal dimensions are computationally heavy. In addition, the suggested method suffers from the fact that the degree of both hypnosis and analgesia affect the fractal dimension. The orthogonality of the two measures corresponding to the cortical and subcortical activity is thus poor. Although the method was primarily suggested for measuring the hypnosis of the patient, it is probable that it will also correlate with the degree of the surgical stress, which increases hemodynamic instabilities and the fractal dimension of the RRI series. Using this method, it is thus difficult to tell, whether the anesthetist should add or reduce opioids or hypnotic drugs.

European patent application EP1273265 describes a simpler method for analyzing an RRI and a blood pressure (BP) time series. Furthermore, the method tries to make a clear distinction between the sympathetical and parasympathetical cardiovascular responses. The sympathetical responses correlating with the surgical stress increase the heart rate and blood pressure. The acceleration index of the heart rate and the index for the increase of the blood pressure is calculated using a filter, a kind of edge filter, which detects the increasing slopes in the values of RRI or BP, but neglects the decreasing values. The document suggests that these indices may be used as a measure of the adequacy of analgesia. However, the method lacks the specificity to noxious stimuli and detects also the variations caused by respiration and other increasing slopes resulting from normal sympathetical activation without noxious stimulation. For instance, when the patient is in light anesthesia, both the sympathetical and parasympathetical branch of the ANS is active and the indices show erroneously high values suggesting insufficient analgesia.

The prior art technologies thus aim to describe the adequacy of anesthesia using a unidimensional concept for the depth of anesthesia. They do not account for separate hypnotic and analgesic components, which are orthogonal, i.e. as much independent of each other as possible, and specific to the hypnotic and analgesic medications given during anesthesia. Thus the prior art methods cannot not answer to the question, whether one should add or reduce the analgesics or hypnotics in order to restore a balanced anesthesia. All prior art technologies that are claimed to measure the adequacy of analgesia show a considerable dependence on the level of hypnosis and, consequently, at light anesthesia without any noxious stimulations show a value that is usually associated with poor analgesia. A further drawback of the prior art technologies is that the measurement values show a considerable inter-patient variability. This makes their interpretation, i.e. the interpretation of the adequacy of anesthesia, difficult.

The present invention seeks to alleviate or eliminate the above drawbacks associated with the above-described measurements and to bring about a mechanism for monitoring and evaluating the analgesic component required for accomplishing optimal pain relief and balanced anesthesia.

SUMMARY OF THE INVENTION

The present invention seeks to provide a novel mechanism for monitoring pain-related responses in a patient. Pain-related responses may be detected as activity in the sympathetical branch of the ANS of the patient or as increased motoric activity, especially in facial mimic muscles. The responses are also indicative of the quality of analgesia and may be used for accomplishing optimal pain relief for balanced anesthesia, for example. The invention further seeks to provide a mechanism, which is usable for monitoring the quality of analgesia in diversified situations regardless of inter-patient variability, regardless of the physiological signal being utilized, regardless of the current treatment of the patient, such as the current phase of a surgery, and also regardless of the level of hypnosis of the patient. The invention further seeks to provide a mechanism that allows the levels of hypnosis and analgesia to be evaluated reliably and independently of each other.

In the present invention, the values of a first measurement signal obtained from the patient are first normalized in order to obtain a normalized measurement signal whose values are within a predetermined value range that is the same for all patients. The first measurement signal may be a physiological signal measured from the patient, such as an RRI signal, but it may also be a signal representing a variable refined from one or more physiological signals measured from the patient. A second measurement signal indicative of a pain-related activity in the patient is then taken into use. Although pain-related activities in the patient may relate to increased motoric activity, they most often relate to the activation of the sympathetical branch of the autonomic nervous system. Consequently, the second measurement signal is typically obtained by deriving or extracting from the normalized measurement signal a signal component indicative of activity in the sympathetical branch of the autonomic nervous system. However, if the normalized signal indicates the pain-related activity well enough, it may also be used directly as the second measurement signal. This applies especially to a case where the first measurement signal is an EMG signal or a signal derived from an EMG signal. A threshold condition is then set based on the normalized signal for the second measurement signal, and the rate at which the second measurement signal fulfills the threshold condition is monitored. Pain is then detected, if the fulfillment rate exceeds a certain limit. The fulfillment rate may be measured as the number of times that the second measurement signal fulfills the threshold condition within a time unit, or as the proportion of time that the threshold condition remains fulfilled by the second measurement signal.

Several first measurement signals of different types may also be utilized, in which case several normalized signals and second measurement signals are obtained, correspondingly. In this case the threshold condition includes a requirement for each of the second measurement signals, whereas in case of a single first measurement signal the threshold condition may simply be a single threshold value. Based on the monitoring, the system of the invention may then output a signal indicative of the pain experienced by the patient.

Thus one aspect of the invention is providing a method for monitoring pain-related responses in a patient. The method includes acquiring at least one first measurement signal from a patient and transforming at least one of the at least one first measurement signal into a normalized signal having a predetermined value range, whereby at least one normalized signal is obtained. The method further includes setting, based on the at least one normalized signal, a threshold condition and monitoring a rate at which at least one second measurement signal fulfills the threshold condition, wherein each of the at least one second measurement signal is derivable from a corresponding normalized signal and indicative of pain-related activity in the patient.

Another aspect of the invention is that of providing an apparatus for monitoring pain-related responses in a patient. The apparatus includes first means for acquiring at least one first measurement signal from a patient and transformation means for transforming at least one of the at least one first measurement signal into a normalized signal having a predetermined value range, whereby at least one normalized signal is obtained. The apparatus further includes second means for setting a threshold condition based on the at least one normalized signal and third means for monitoring a rate at which at least one second measurement signal fulfills the threshold condition, wherein each of the at least one second measurement signal is derivable from a corresponding normalized signal and indicative of pain-related activity in the patient.

The invention is usable both at light and deep levels of sedation and anesthesia. At light levels of sedation or anesthesia, most of the sympathetical events are originated from other than noxious stimulations, whereas at deep levels only noxious stimulations are strong enough to evoke responses. Because the threshold value may be determined based on signal value statistics in the past, including even all responses, and because the non-noxious responses usually are smaller than the responses to stronger noxious stimulations, normal arousals are either not detected or their contribution remains low.

As mentioned above, in one embodiment of the invention several physiological signals of different types may be utilized. When a combination of physiological signals is used, the performance over full sedation range may be improved.

The method of the invention adapts both to changes in the level of a particular physiological signal, which may depend on the patient in question, and to changes in the level of a physiological signal obtained from a particular patient, which may depend on the course of a surgery, for example. Furthermore, the method of the invention adapts to artificial changes in the signal. These may originate, for instance, from a change in the attachment of a sensor or electrode on the skin, resulting in either smaller or larger signal amplitudes. Similar artifacts may be caused, for instance, by a change in ventilator settings, which may considerably affect the respiration modulation in the physiological signal. Because the normalization can adapt to any changes in a time window longer than the length of the input buffer used for the normalization transformation, the effects of the artifacts are only transitional in the final result obtained by the method. However, without the normalization manual measurement adjustments or complicated algorithmic adjustments would be needed.

The method of the invention is especially suitable for use in connection with an expert system, which may output a variety of different indices or one index with a changing information content. For instance, if patient relaxation is induced using NMBAs, which also affect the fEMG signal on the forehead, which is one of the signals indicative of pain-related activity, the combination of the physiological signals utilized should be altered by omitting the fEMG signal. This would normally cause troubles in adapting to the new combination of physiological signals. However, due to the normalization transformation the system of the invention can rapidly adapt to the new situation.

By means of the invention, the level of hypnosis and the level of analgesia may be presented as two separate index values both varying between two fixed values, such as zero and one hundred, wherein zero is indicative of too strong a medication and one hundred of too mild a medication, or vice versa.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIGS. 1 and 10 in the appended drawings, wherein.

DETAILED DESCRIPTION OF THE INVENTION

Figure 1:
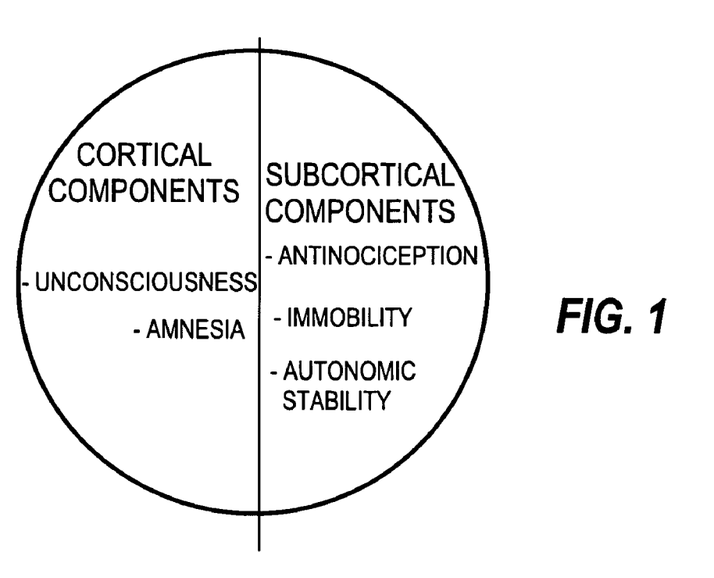
FIG. 1 illustrates the concept of the quality of anesthesia.

FIG. 1 illustrates the concept of the quality of anesthesia. According to the current comprehension, the quality of anesthesia includes five different components: hypnosis (i.e. unconsciousness), amnesia, antinociception, immobility, and the stability of the ANS. The first two components, the hypnosis and amnesia, are of cortical origin and are indicative of cortical activities. The suppression of the cortical activity is obtained by drugs, which typically affect neural signaling globally in the brain. The drugs may activate the natural inhibitory GABA (gamma-aminobutyric acid) receptor system in the brains or prevent, by an unknown mechanism, neural signaling in the synapses between the neurons. For this reason, the drugs often also affect other parts than the cortex in the brain, thereby also suppressing subcortical activity.

The other components in the anesthesia model, which are indicative of sub-cortex related activity in the patient, are much more specific and often relate to altering, modulating or disturbing neural signaling at certain receptor or neurotransmitter level. These components can be affected selectively by different specific drugs. For instance, antinociception, i.e. the suppression of the neural transmission in the pain pathways, is achieved by opioid drugs, which affect the opioid/enkephalin receptors and activate the descending pathways, which block or modulate the nociceptive stimuli in the spinal cord. Furthermore, the NMBA drugs block the neural transmission in peripheral neuro-muscular junctions, which results in one kind of specific immobility of a patient. The stability of the ANS and the antinociception are closely related, since noxious stimulation in deep anesthesia causes hemodynamic and hormonal instability. The stability of the ANS is therefore also advanced by opioid drugs and by several other drugs, which may affect specifically the parasympathetical or sympathetical activities of the ANS.

Although many drugs may be involved in achieving an adequate level of the cortical and subcortical activity, the adequacy of anesthesia is often managed only by a gas anesthetic agent or other hypnotic agent, which dominantly (and globally) affects the cortical activity, and by an opioid, which selectively modulates the pain pathways at subcortical level, and by a NMBA drug, which induces immobility in peripheral nerve-muscle junctions. The effects of the hypnotic agent may be monitored, for instance, by the above-described methods based on calculation of spectral entropy and the neuromuscular blockade by an NMT (NeuroMuscular Transmission) measurement. The hypnotic and NMBA drugs can then be administered based on these measurements. The present invention provides a mechanism for measuring the sympathetical activity in the ANS of a patient in order to be able to assess the pain experienced by the patient and to deliver analgesic drugs based on the pain indicated by the measurement.

Figure 2:
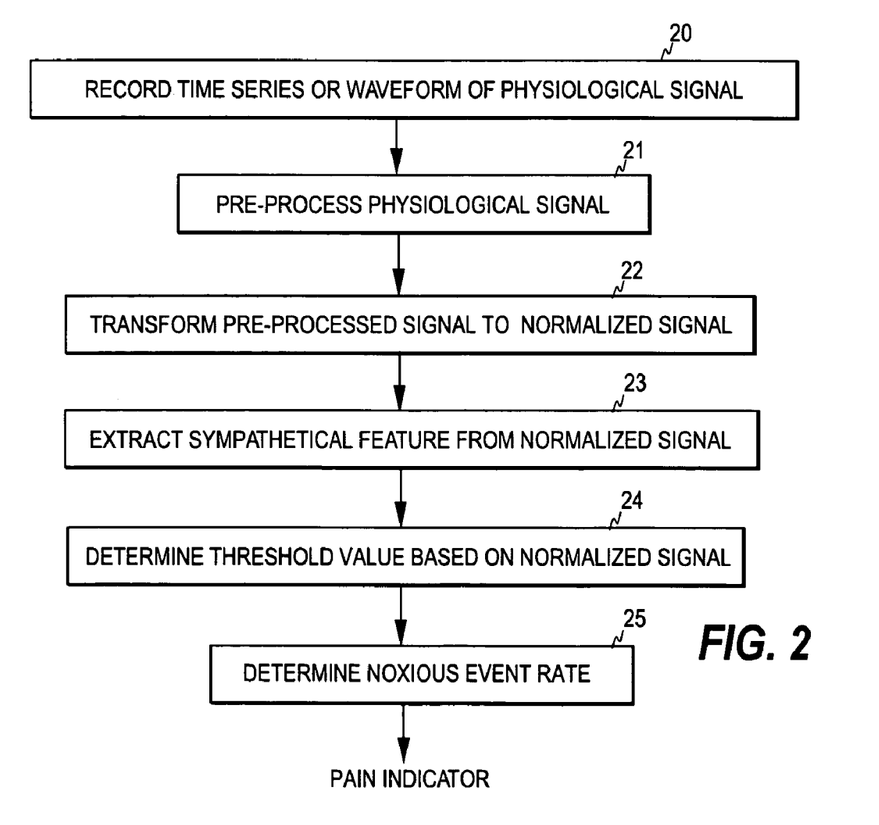
FIG. 2 is a flow diagram illustrating one embodiment of the present invention.

FIG. 2 illustrates one embodiment of the present invention. For the actual measurement, signal data is first obtained from the patient (step 20). This may be implemented in a conventional manner, i.e. while the patient connected to the patient monitoring system, a physiological signal is recorded and stored in a memory of a monitoring device. The physiological signal may be, for example, an ECG, waveform or a photoplethysmographic, a blood pressure or a respiration waveform, or a signal representing a physiological trend parameter, such as heart rate, pulse rate, systolic, diastolic or mean blood pressure. The physiological signal may also be an (f)EMG signal or a skin conductivity signal. Typically, waveforms are sampled at about 100 samples/sec, and the trend parameters effectively at a rate of about 10 samples in a minute.

The recorded signal data may then be pre-processed at step 21 for extracting the parameters that are not directly available as a trend parameter, such as beat-to-beat or cycle-to-cycle intervals of the waveform. For instance, to obtain an RRI signal the moments at which the R-peaks occur in the QRS-complex are extracted from an ECG waveform, and the R-to-R intervals are recorded. In case of a plethysmographic waveform, the pulse amplitude may be extracted for each pulse beat.

A time series is then formed from the extracted parameters. As the invention aims to assess the subcortical integrity of the autonomic and/or motoric functions by measuring the responsiveness of the system, it is sometimes advantageous to examine the changes of the signal instead of the absolute amplitudes or intervals as such. Therefore, the time series of the physiological parameter may be pre-processed by derivation of the signal in order to enhance fast changes and responses. This is especially important in the analysis of plethysmographic amplitudes, in which slow changes may be associated with fluid balance, change of attitude or temperature, or with slow hormonal control of the body. The pre-processing phase, i.e. step 21, may also include filtering out of some of the frequency components of the signal or rejecting artifacts, as well as correcting or removing some of the values of the signal, such as ectopic beats of the ECG wave.

From the pre-processing phase, a sequence of signal values representing a physiological signal or parameter is thus obtained. In the following this sequence is also termed the first measurement signal.

One of the requirements for the method of the invention is that it shall be suitable for different patients and patient groups, such as children and adults, who may respond in different ways to the surgical stress they are imposed in. In practice, the normal heart rate, for example, may vary from 40 to 150 beats/min, and the variability of the heart beat interval tends to decrease considerably with the age of the patient. Furthermore, during a surgery different medications affect the absolute values of the physiological signal, which, therefore, are unreliable alone for assessing the sympathetical activation in the ANS. Therefore, the method of the invention includes a normalization of the physiological signal or parameter examined.

In the normalization, the first measurement signal is transformed into a signal that has a predetermined value range and predetermined distribution characteristics for all patients (step 22). The transformation thus "forces" the values of the first measurement signal to a certain value range regardless of the values of the input signal.

Figure 3:
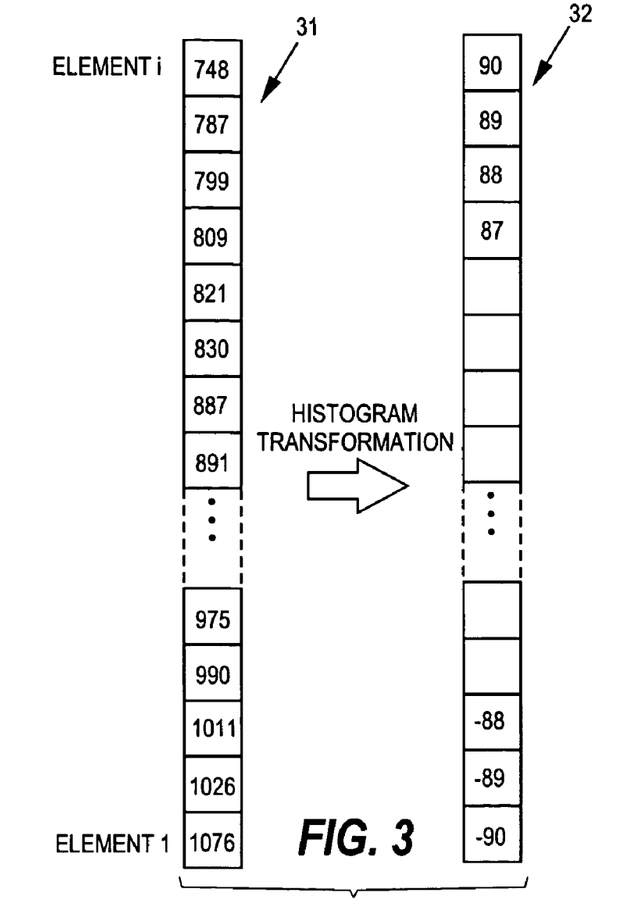
FIG. 3 illustrates one embodiment of the normalization process according to the invention.

The normalization may be performed by means of a histogram transformation, which is illustrated in FIG. 3. In the histogram transformation, an input array 31 and an output array 32 are formed. The input array (buffer) comprises i input elements, also termed bins, storing, respectively, i input values sorted in ascending or descending order, while the output array (buffer) comprises fixed index values sorted in ascending or descending order and stored in i output elements. In the example of FIG. 3, the index values of the output buffer range from −90 to +90 corresponding to the total number of values in the input buffer, i.e. i=181. The signal values obtained from the pre-processing phase are forced to the value range of the output buffer. This may be implemented in three different ways depending on whether full adaptation, partial adaptation, or no adaptation to the incoming signal is utilized. These embodiments of the histogram transformation are discussed in the following.

In full adaptation, the latest signal values of the first measurement signal are stored in the input array so that the value of each new data point obtained from the pre-processing phase replaces the oldest value in the input array. When a new value is obtained from the pre-processing phase, the oldest value in the input array is deleted, and the remaining values and the new value are sorted to form a new input array. The output value of the transformation is then obtained by means of the output array as the index value that corresponds to the location of the new value in the input array. In other words, if the new value is stored in the $k^{th}$ ($k \leq i$) element in the sorted input array, the output value is the index value stored in the $k^{th}$ element of the output array. FIG. 3 shows the R-to-R intervals (RRIs) obtained from an ECG signal, each RRI value indicating the time interval in milliseconds between two consecutive R-peaks of an ECG signal. If full adaptation is utilized, the value of each new data point obtained from the original RRI signal thus replaces the oldest value in the input array. In this way, the level of the signal may change but the output values remain between the lowest and highest indices. The time series obtained from the output array 32 may thus be such that the mean value is constant and the variability of the parameter is limited to a certain range and certain distribution around the mean value. For instance, a Gaussian or even distribution with zero mean value may be used for the values output from the transformation.

In case no adaptation to the incoming signal is used in the transformation, the input array remains the same regardless of the incoming signal values. The input array may be formed based on values measured from a large patient group, which yields a wider distribution of input values. Thus, instead of storing the latest i values of the same patient, the input array may store i fixed values representing the distribution of the values of the first measurement signal among a (large) group of patients. When a new value is obtained from the pre-processing phase, the output value of the transformation is then obtained in the above-described manner as the index value that corresponds to the location of the new value in the sorted input array.

Partial adaptation to the incoming signal refers to the combination of the above two methods. For example, in the partial adaptation two input arrays may be used, one adapting fully to the incoming signal and the other being a fixed array storing values measured from a group of patients. Based on the two input arrays, a combined input array may be formed. When a new value is obtained from the pre-processing phase, the output value of the transformation is then obtained by means of the output array as the index value that corresponds to the location of the new value in the combined input array. The combined input array may be formed in various ways. For example, the two input arrays may have the same length as the output array and the values of the combined input array may be obtained by first sorting the input values and then down-sampling them by taking only every second element to the combined input array. The summed length of two input arrays may also correspond to the length of the output array, in which case the combined input array may be obtained simply by taking the values of both input arrays and sorting them in desired order. For example, the length of each input array may be i elements, if the length of the output array is 2i elements. One input array may then include i reference values obtained from a large patient group, the values having even intervals, for example, while the other input array may includes i latest values of the incoming first measurement signal. The values of the two input arrays are then sorted, for each new value of the incoming signal, in descending or ascending order to obtain the combined input array that indicates the index value corresponding to the current value of the incoming signal.

Figure 4A:
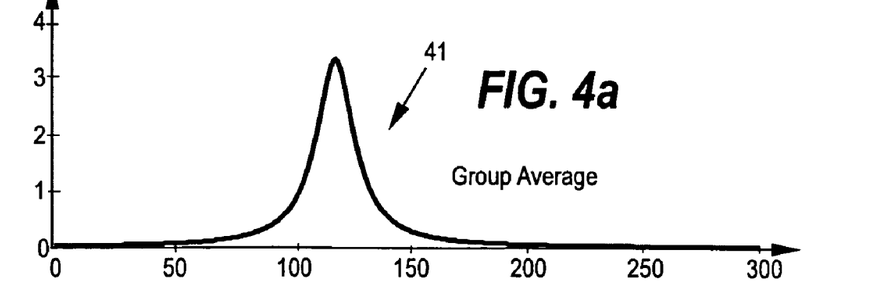
FIG. 4a to 4d illustrate another embodiment of the normalization process of the invention.
Figure 4B:
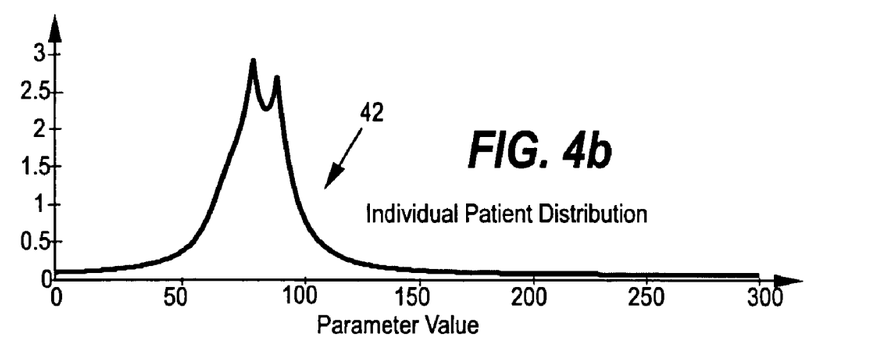

A further embodiment of the partial adaptation is illustrated in FIGS. 4a to 4d. FIG. 4a illustrates a parameter distribution curve 41 for a large number of patients representing a certain patient group in general anesthesia. The size of the patient group may be very large representing about 1000 patients, for example. The range of the parameter values, in the figures from 0 to 300, is advantageously selected to be much wider than the actual range obtained during a surgery of an individual patient. During the surgery the same parameter is then measured and a histogram distribution is created using the same parameter value bins. This distribution for the individual patient may contain a fixed number of values, e.g. 300, and the distribution may be updated using the full adaptation method described above. It is also possible that a cumulative distribution of the parameter values of the individual patient is collected and that the so obtained distribution counts are scaled down to a predetermined match in total counts to the patient group distribution. In such a case, the individual patient distribution may represent the parameter values since the beginning of the surgery till the current moment during surgery. An example of a normalized patient-specific distribution curve 42 obtained during a surgery is presented in FIG. 4b.

Figure 4C:
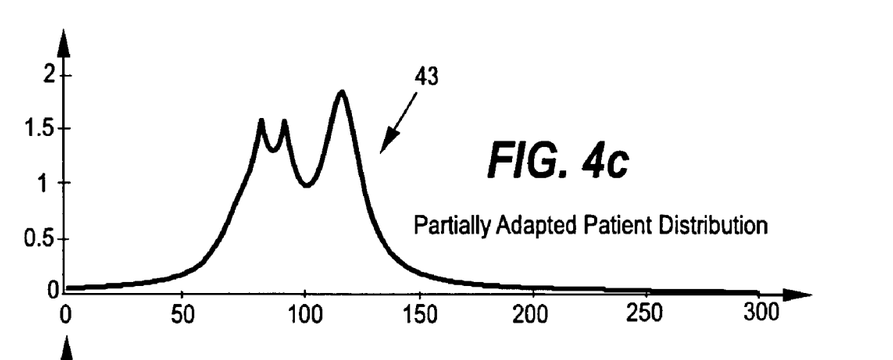
Figure 4D:
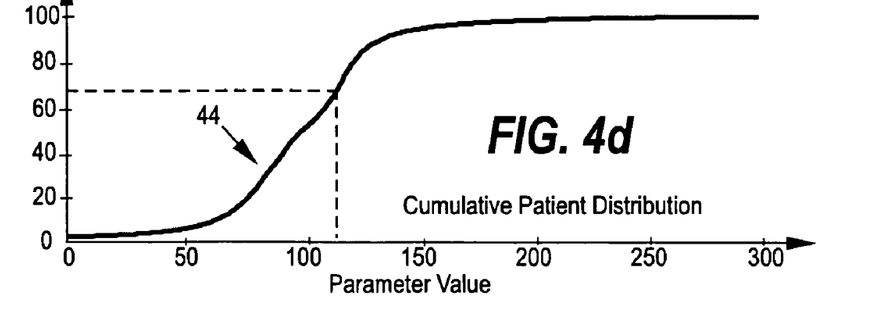

The normalized patient-specific distribution is then added in a predetermined proportion to the normalized patient group distribution, and an average total distribution curve 43 is formed, as shown in FIG. 4c. In this example, the two normalized distributions are weighted equally in the total distribution. For calculating the input parameter value array for the partially adapted histogram transformation a cumulative sum of the average total distribution is then constructed as shown in FIG. 4d. If the histogram transformation arrays are 101 element long, for example, the new values for the input bins of the histogram transformation can be obtained by projecting the cumulative sum values 0, 1, 2, . . . , 100 of the Y-axis to the parameter value axis (X-axis), as is shown by dashed lines in FIG. 4d. The X-axis values obtained in this way form the input values of the input array for the histogram transformation. The actual histogram transformation is then executed without adaptation. In this embodiment, input values for the input array are thus obtained by adding a group distribution curve to the patient-specific distribution curve and then defining the input values for the input array by means of the cumulative distribution function of the summed distribution curve. Once being defined in the above-described manner, the input values of the input array remain fixed for a predetermined update interval, which can typically represent about 100 new individual parameter values.

The proportions of the adaptive and non-adaptive values in the combined input may vary. The same applies to the size of the steps between consecutive (fixed) values stored in the input or output arrays. For example, in the example presented in connection with FIGS. 4a to 4d each consecutive input array bin contained one percent of the input values. However, the steps may also be such that a certain other percentage of values is within each step (i.e. in each bin), in which case the step may be smaller around one range of the input values and correspondingly larger around another range of the input values.

Partial adaptation to the incoming signal may also be accomplished so that only every $i^{th}$ (i=2, 3, 4 . . . ) new data point obtained from the pre-processing phase replaces the oldest value in the input array. In this way, the input array values originate from further in the past. The update procedure chosen thus controls the length of the memory for the adaptation to the signal.

The median value of the output signal, i.e. the center index of the output array, is usually transformed to zero output. The distribution of the output values can be specified according to the needs of the application. In counting of noxious events, which is discussed below, it is advantageous that the output distribution is Gaussian, in which case the counting threshold can be selected to be proportional to the standard deviation of the output values obtained from the transformation.

An individual physiological parameter is seldom normally distributed around the mean value. The histogram transformation has therefore two clear advantages. First, all patients are initially set to the same mean and variability of a particular physiological signal or parameter, and, second, during changing conditions, such as changing patient medication or sensor attachment, the parameter output maintains the mean and variability in the predetermined scale determined by the histogram transformation. The sympathetical nociceptive responses appear then as values that reach the tail regions of the normalized value range, independently of the patient or of the conditions, such as the phase of the surgery. Other responses and normal modulations of the signal in turn occur in the center part of the variability range, as such changes are also more common. The histogram transformation is thus especially suitable for counting noxious events or sympathetical responses, which appear as the largest deviations from the mean value of the signal.

The histogram transformation conserves the frequencies and fractal properties of the original time series. In the full or partial adaptation, large amplitude bursts tend to suppress subsequent signal fluctuations having low amplitudes. The total spectral power of the normalized output signal is then also conserved. In this case the method is particularly suitable for comparing the signal power on different frequency bands, such as for examining the sympatho-vagal balance (LF/HF) in a HRV analysis.

Referring to FIG. 2 again, in the next step of the embodiment of FIG. 2, a pain-related feature indicative of nociception is extracted from the normalized signal (step 23). In this context, the signal representing the pain-related feature is also termed a second measurement signal. Although in case of an fEMG signal the pain-related feature is the power of the EMG signal, the pain-related feature relates most often to the activation of the sympathetical branch of the autonomic nervous system. Sympathetical activations appear in various signals in a characteristic way depending on the signal in question: sympathetical activation accelerates the heart rate, increases blood pressure, and constricts the blood vessels, for example. In comparison, parasympathetical responses show up in the opposite manner. Furthermore, the sympathetical responses occur with a delay of a few seconds, while the parasympathetical responses may appear more or less immediately and they are alone responsible for all variations, which have the frequency range higher than about 0.15 Hz. The sympathetical branch of the ANS may activate variations with periods longer than about 10 sec. These low frequency components of the variability of the physiological signal or parameter are thus mainly associated with sympathetical regulation, although parasympathetical regulation is also typically involved. A typical sympathetical or noxious response pattern in a physiological parameter is such that immediately after the stimulus a parasympathetical withdrawal may first take place, after which the sympathetical activation takes over, and the change in the signal continues in the same direction. Therefore, a noxious response may include initial fast components due to the switching off of the parasympathetical branch of the ANS. This, when repeated, leads to beat-to-beat irregularities in the cardiac-related physiological signal. The delayed and continuing activation of the sympathetical nervous system eventually results in a change in the absolute level of the parameter value itself. The pain-related feature in the physiological parameter may thus appear either as fast changes, i.e. as beat-to-beat irregularities, or as a slower change in the absolute level of the parameter, which recovers later. The parasympathetic regulation is often responsible for rather fast regular rhythms, such as respiration modulation of the physiological parameter value. A characteristic feature of a dominating parasympathetic control is regularity and overall constancy in the signal. Parasympathetical regulation also restores the normal functions after sympathetical overactivation. This rather simple picture of the ANS regulation is actually much more complicated, because physiological parameters are not independent, but related to each other through various body control mechanisms, such as the baroreflex. If the heart rate increases, the blood pressure increases, if the systemic resistance in the blood vessels remains constant. The baroreflex forms a negative feedback to the system, as it with increasing blood pressure tends to decrease the heart rate, and vice versa, to maintain stable blood pressure.

Very low frequency variations can usually be associated with hormonal regulation of the physiological parameter, with temperature regulation or with normal day-night rhythm or mood, or with activity changes in the person. These very low frequency components are actually harmful when noxious events are to be recognized and counted, and they can be filtered out in the pre-processing phase of the method. However, this can be performed more elegantly in connection with the histogram transformation. Namely, the length of the histogram transformation (i.e. the length of the array) determines the time scale over which the system adapts to the new values of the input signal. Optimally, the length of the transformation is about 2 to 4 minutes. If all the values of the input array are replaced within a cycle of 2 to 4 minutes, slow changes are filtered out, but the other sympathetical and parasympathetical responses are still clearly visible and measurable.

Table 1 lists some of the most useful pain-related features related to various physiological signals, the features being thus indicative of pain experienced by the patient. Apart from the EMG signal all pain-related features in the table are indicative of activity in the sympathetical branch of the ANS.

| Physiological Signal | Pain-related feature |
| --- | --- |
| Heart Rate (HR) | HR acceleration |
| HR | Low Frequency (LF) variability: LF spectral power, LF Standard Deviation (SD2 in Poincare analysis) |
| HR | The ratio of the LF variability to the High Frequency (HF) variability, so called sympatho-vagal ratio. |
| Blood Pressure (BP) | Elevated BP |

-continued

| Physiological Signal | Pain-related feature |
|---|---|
| BP | Low Frequency (LF) variability |
| BP | The ratio of the LF variability to the High Frequency (HF) variability, so called sympatho-vagal ratio. |
| Plethysmographic Amplitude (Pty_A) | Small and decreasing amplitude |
| Pty_A | LF variability |
| Pty_A | The ratio of the LF variability to the HF variability, so called sympatho-vagal ratio. |
| Pty_A | Beat-to-beat variability (Pty_B2B) excluding respiration variability |
| Pty_A | The ratio of Pty_B2B to the regular respiration variability (Pty_HF_Resp) (Pty_B2B/Pty_HF_Resp) |
| fEMG | fEMG power increase |
| SC, Skin Conductivity | Activation of the sweat glands, increase of SC Lacrimation |

At step 23 in the embodiment of FIG. 2, the pain-related feature indicative of pain is thus extracted from the normalized signal. In case of an RRI time series derived from an ECG waveform, for example, the pain-related feature can be seen as the low frequency variability in the inter-beat intervals, which may be extracted by low-pass filtering the normalized signal. In a plethysmographic waveform, in turn, the pain-related feature may be seen as the irregularity of the beat-to-beat amplitude variability. However, the low frequency component of the variability of the inter-beat intervals may also be utilized as the pain-related feature in connection with the plethysmographic waveform.

In the next step of the method (step 24), a threshold value is determined for counting of noxious events. The threshold is a value that determines when a noxious event is detected: when the amplitude of the extracted pain-related feature exceeds the threshold value determined, a noxious event is registered by a counter. The threshold value is a natural consequence of the patient normalization: the threshold value is determined using the output distribution of the histogram transformation. In case of a Gaussian output parameter, the threshold value may be set to a value proportional to the Standard Deviation (SD) on that side of the normal distribution, which is determined by the pain-related feature in question. (When the pain-related feature is a sympathetical feature, the parasympathetical threshold could be correspondingly set to the opposite side of the distribution or in the center part of the distribution curve). If the output distribution is even, the threshold value may be set to a predetermined value on the sympathetical response side of the distribution curve.

It is essential that the threshold is determined based on the variability of the entire physiological signal and that the feature extracted at step 23 is that part of the entire physiological signal, which is associated with sympathetical regulation (or motoric activity in case of an fEMG signal). For instance, when the sympathetical feature is the variability of the LF component of the entire signal over 30 sec, for example, the threshold is determined on the basis of the variability of the entire signal, comprising the LF, HF, and beat-to-beat signals, over a time interval considerably longer than the duration of the sympathetical response indicator. The variabilities of the sympathetical feature and the entire signal may be measured by calculating the standard deviation of the respective signals, for example. A noxious event is then registered when the current value of the sympathetical feature exceeds a certain level of variability in the histogram output array recorded typically over 2 to 4 minutes before the sympathetical reaction. In case the sympathetical feature is an HR acceleration or other quantity related to the increase or decrease of the absolute value of a physiological signal or parameter, the increase or decrease over a short time period is compared to overall changes during the much longer interval of the histogram transformation.

In the next phase (step 25) of the embodiment of FIG. 2, the number of noxious events registered in a time unit of a predetermined length is counted. In other words, the rate at which the amplitude of the pain-related feature exceeds the set threshold is determined. Here, a time unit of about 3 minutes, corresponding to the length of the histogram transformation, may be used. If the rate reaches a certain limit value, pain is detected. In fact, instead of counting the number of events that exceed the threshold value in a time unit, the time portion during which the amplitude of the pain-related feature is higher than the set threshold value, can be summed up. In this case long sympathetical events contribute more to the final value than shorter events. In this context, the monitoring of the rate at which the threshold condition is fulfilled thus covers the above different implementation alternatives, i.e. monitoring the number counts in a time unit or monitoring the said proportion of time that threshold condition is fulfilled.

The determination of the threshold may also be described by means of the above two signals, i.e. the entire physiological signal including all frequencies and the pain-related feature, which is a component of the entire physiological signal. The threshold value for an elevated pain-related activity is determined from the history of the entire physiological signal by first transforming the entire physiological signal to Gaussian statistics over a certain relatively long time interval, such as 2 to 4 minutes, and then determining a threshold value based on the current Gaussian distribution of the entire physiological signal. The count value for the pain-related activity may then be determined as the time fraction during which the pain-related feature, i.e. the extracted signal component, exceeds the threshold value. When the amplitude of the pain-related feature is relatively weak in comparison to the amplitude of the entire signal, the count value, i.e. the monitored rate, is low. But if the pain-related feature is strong, the count value is high, because the amplitude of the pain-related feature is about the same as the amplitude of the entire signal, in which case the Gaussian signal threshold is exceeded often. The count value is thus indicative of the proportion of the pain-related feature in the entire physiological signal.

Figure 5:
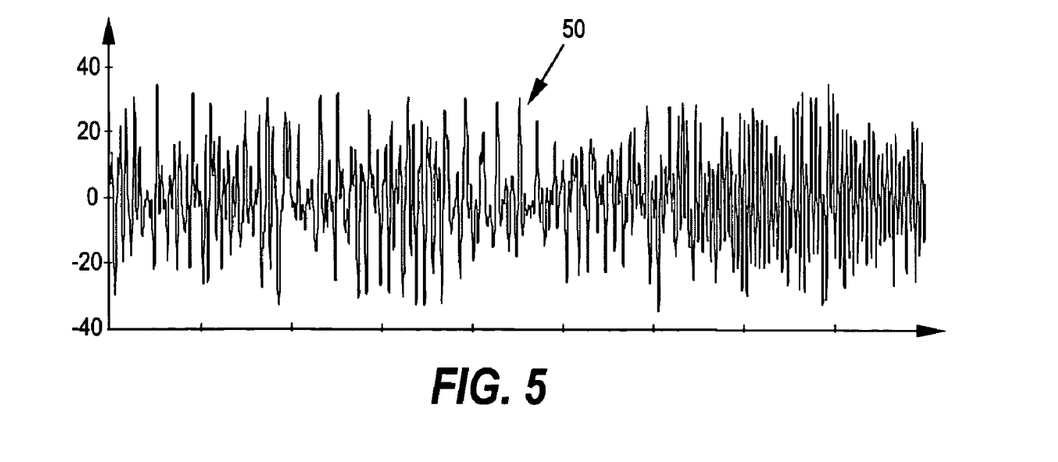
FIG. 5 illustrates an example of a normalized plethysmographic signal.
Figure 6:
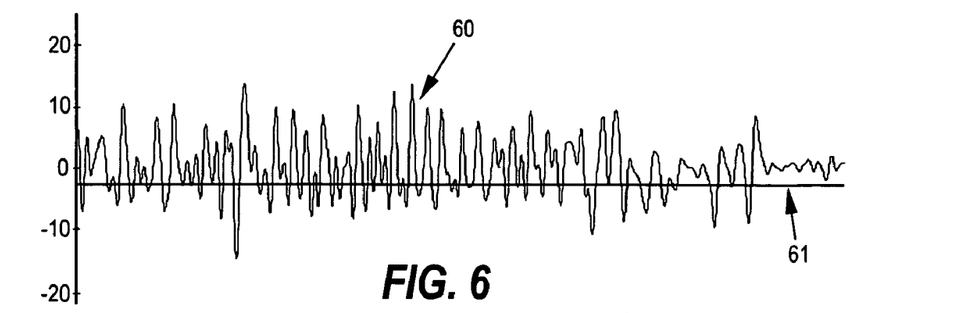
FIG. 6 illustrates an example of the second measurement signal extracted from the normalized signal of FIG. 5, and the threshold defined for detecting noxious events.
Figure 7:
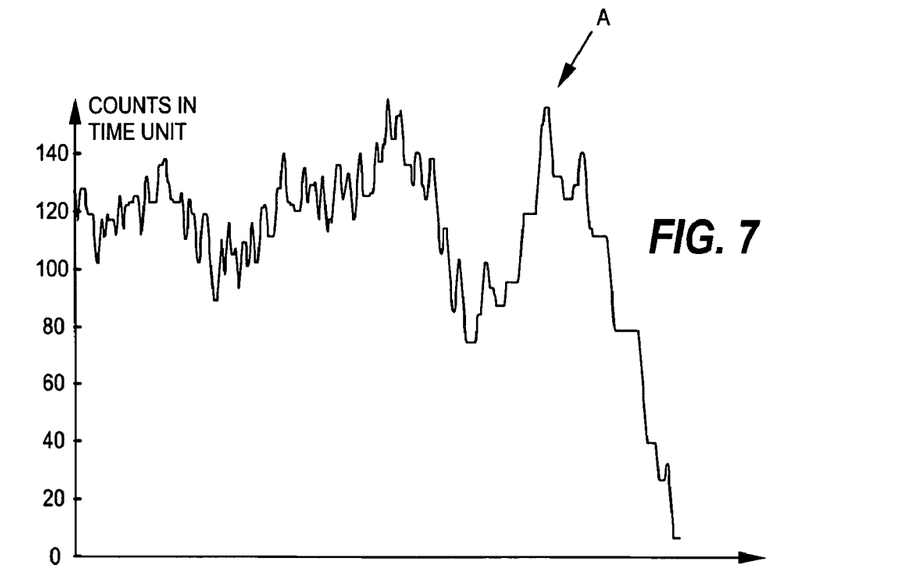
FIG. 7 illustrates a curve representing the noxious events detected in a time unit.

FIGS. 5 to 7 illustrate an example of the above-described extracting and counting steps of the invention. FIG. 5 shows a plethysmographic amplitude signal 50 obtained from the histogram transformation. This is thus the entire plethysmographic amplitude signal including all frequency components. When the pain-related feature indicative of pain is extracted from the entire signal by filtering, for example, signal 60 shown in FIG. 6 is obtained. As can be seen, the higher frequency components present in the entire signal 50 are no more present in the extracted signal. Based on the entire signal, a threshold 61 is then determined for the extracted signal. In this example, the threshold corresponds to about −1 Standard Deviation of the entire signal. The side of the normal distribution corresponding to the pain-related (sympathetical) feature is thus the side below the mean value. Therefore, a noxious event is detected when the value of signal 60 falls below threshold 61, i.e. when the plethysmographic amplitude decreases suddenly.

FIG. 7 illustrates an example of the count values obtained at step 25. The figure shows a point A, where the infusion of an analgetic is started. As can be seen, the count value clearly responds to the infusion. The lower the count the better the antinociception due to the pain relieving drug. In one embodiment of the invention, the pain-related count value obtained at step 25 is further normalized to a fixed range, such as between 0 and 100. In this context, this normalized value is called the index of analgesia. The normalization may again be implemented by employing a histogram transformation, in which the output count array may be a linear array from 0 to 100 and the input array a 101 element array of the count values of a large patient group, for example. The output count value, i.e. the result from the second histogram transformation, is then the array index corresponding to the location of the latest pain-related count in the input array. The input count array is optimally updated in a way that allows the first output value to be obtained sooner than the array is full. Non-adaptive, partial adaptive or fully adaptive input arrays can be used. The index of analgesia may be used to control the infusion of analgetics, as is shown in connection with FIG. 11 below.

In one embodiment of the invention, histogram transformations may thus be computed at two different phases. The first transformation phase is the above-described transformation of the pre-processed physiological signal into a normalized signal, while the second transformation phase is for transforming the count values to the indices of analgesia.

Figure 8:
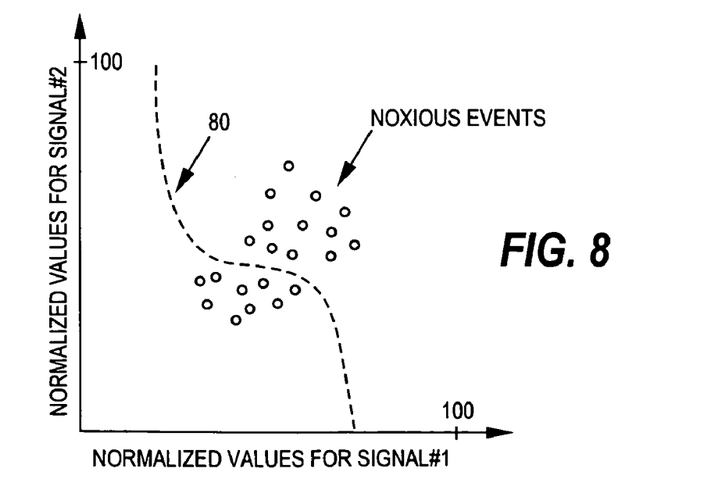
FIG. 8 illustrates the use of two different measurement signals for the monitoring of noxious events.

A further aspect of the invention is that the index of analgesia may be made specific to noxious events, i.e. counting of responses to non-noxious stimulations may be omitted. However, as one physiological parameter alone is seldom specific to a noxious event, in one embodiment of the invention a combination of physiological signals may be used instead. FIG. 8 illustrates an embodiment in which two physiological signals are utilized. Both signals may be pre-processed and normalized independently as described above in connection with steps 21 and 22, respectively, and a pain-related feature is extracted from both signals. The threshold condition determined for the event counting may then be defined by a curve 80 in the xy-plane, where the normalized values of the first physiological signal are on the x-axis and the normalized values of the second physiological signal on the y-axis. Each event when a value pair of the pain-related features (i.e. simultaneous values of the pain-related features) is on the desired side of the curve is then registered as a noxious event. If the rate of the noxious events exceeds a certain limit, pain is detected.

The number N of the physiological signals utilized may thus be greater than one (N>1), in which case each signal is normalized separately. If the N simultaneous normalized values fulfill a predetermined threshold condition, a noxious event is registered. The threshold condition is defined by a surface in an N dimensional space. If the signal values penetrate the surface or are on a predetermined side of the surface, noxious event is registered. The rate obtained may then be transformed to the index of analgesia.

In another embodiment of the invention, the actual physiological signal(s) is/are not normalized directly, but a pain index signal is first calculated based on one or more of the physiological signals in the pre-processing phase and the pain index signal is then normalized in the above-described manner in order to obtain normalized pain index values. The pain index signal may be calculated, for example, based on one or more physiological signals in the set including an RRI signal, a plethysmographic amplitude signal, and an EMG signal. This embodiment of the invention is particularly suitable, when the pain index signal is of a counter type in the sense that it reacts to each noxious event, but does not maintain the elevated index values for longer periods. A component indicative of pain-related activity is then a short bump pattern in the pain index signal. These patterns may be extracted from the normalized pain index signal, and a threshold is determined for the component based on the entire history of the normalized pain index signal. The method is thus the same as discussed above but a variable derived from one or more physiological signals is used instead of the said signals as the first measurement signal.

In a further embodiment of the invention, non-noxious responses indicative of patient comfort may be monitored, either instead of or in addition to noxious responses. In an embodiment utilizing only non-noxious responses, the normalized signal is acquired as described above. However, the signal component extracted from the normalized signal is in this case indicative of inactivity, rather then activity, in the sympathetic branch of the ANS. Thus, as long as the monitored rate is above the set limit, no pain is detected. Pain may thus also be detected based on a signal that is indicative of a painless state. Noxious and non-noxious responses may also be used together to get an image of the pain experienced by the patient. Since only non-noxious responses may be monitored to detect pain, it is to be understood that the extracting of a measurement signal indicative of activity in the sympathetical nervous system also covers extracting of a measurement signal which indicates activity by indicating low inactivity in the sympathetical nervous system.

Figure 9:
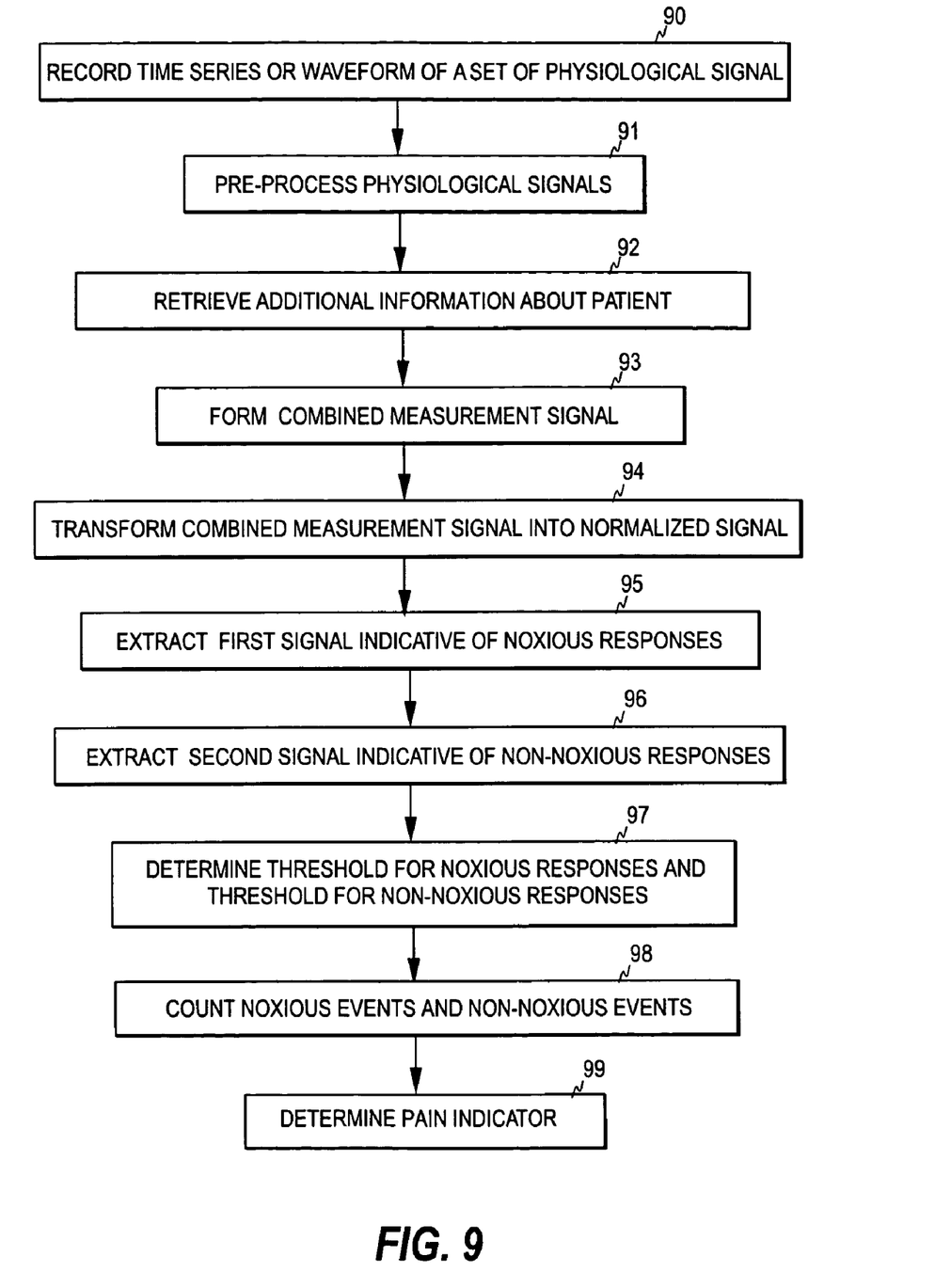
FIG. 9 is a flow diagram illustrating another embodiment of the present invention.

FIG. 9 illustrates one embodiment in which both noxious and non-noxious events are registered. In this embodiment, a set of physiological signals is first acquired and each signal is pre-processed to obtain a desired set of measurement signals (steps 90 and 91). Then, additional information of the patient is retrieved at step 92. This information may include, for example, information about the current medication of the patient, which may render one or more of the measurement signals in the set useless or less useful. Based on the information, a combined measurement signal is then formed at step 93. As discussed above, the combined measurement signal may include a set of measurement signals or parameters, or an index signal derived based on one or more of the measurement signals in the set. The combined measurement signal is then normalized by a histogram transformation in order to obtain a normalized measurement signal (step 94). From the normalized measurement signal two signal components are then extracted: a first signal indicative of noxious responses and a second signal indicative of non-noxious responses (steps 95 and 96). Based on the entire normalized signal a separate threshold is then determined for both signal components (step 97). Based on the thresholds, the system then counts both the noxious and non-noxious events (step 98). Based on the counts, a variable indicative of pain may then be calculated (step 99).

In the above embodiments, the pain-related feature, i.e. the second measurement signal, was obtained by extracting it from the corresponding normalized signal. However, in some cases the normalized signal(s) as such may be sufficient for obtaining an indication of pain-related activity in the patient. In these cases the normalized signal(s) may be utilized directly as the second measurement signal(s), without separately extracting the second measurement signal from the normalized signal. This applies especially to a case where the first measurement signal is an EMG signal or a signal derived from an EMG signal.

Figure 10:
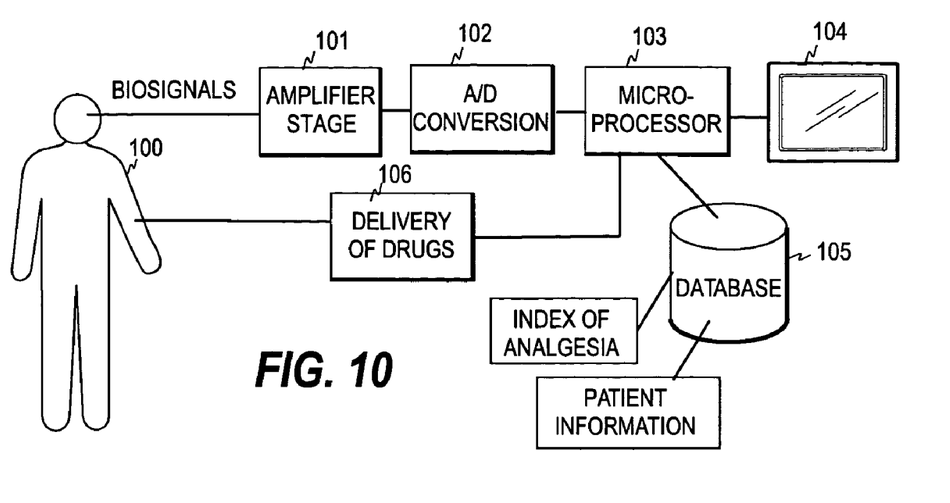
FIG. 10 illustrates one embodiment of a system according to the invention.

FIG. 10 illustrates one embodiment of the system according to the invention. The biosignals obtained from one or more sensors attached to a patient 100 are supplied to an amplifier stage 101, which amplifies the signals before they are sampled and converted into digitized format in an A/D converter 102. The digitized signals are supplied to a microprocessor 113 which may then record the signals.

The microprocessor is provided with a database or memory unit 105 holding the digitized signal data obtained from the sensor(s). The microprocessor may perform the above-described pre-processing phase and form a combined measurement signal, if such a signal is utilized. The microprocessor may also retrieve patient information from the memory unit in order to omit some of the signals or to give them less weight when forming the combined signal. The microprocessor may further perform the histogram transformation to obtain one or more normalized signals, extract the signal(s) indicative of noxious and/or non-noxious responses from the normalized signal(s), define the threshold(s) for the noxious and/or non-noxious responses, and determine a pain indicator based on the responses registered. Although one processor may perform the above steps, the processing of the data may also be distributed among different processors (servers) within a network, such as a hospital LAN (local area network).

The microprocessor may display the results on the screen of a monitor 104 connected to the microprocessor, and it may further supply the calculated pain indicator, such as the index of analgesia, as input data to a device or system 106 delivering drugs to the patient, which enables automatic control of the pain state of the patient (cf. FIG. 7).

Although the invention was described above with reference to the examples shown in the appended drawings, it is obvious that the invention is not limited to these, but may be modified by those skilled in the art without departing from the scope and spirit of the invention.

The invention claimed is:

1. A method for monitoring pain-related responses in a patient, the method comprising the steps of:
    acquiring at least one first measurement signal from a patient;
    transforming at least one of the at least one first measurement signal into a normalized signal having a predetermined value range, whereby at least one normalized signal is obtained;
    based on the at least one normalized signal, setting a threshold condition; and
    monitoring a rate at which at least one second measurement signal fulfills the threshold condition, wherein each of the at least one second measurement signal is derivable from a corresponding normalized signal and indicative of pain-related activity in the patient.

2. A method according to claim 1, wherein the monitoring step includes using the at least one normalized signal as the at least one second measurement signal.

3. A method according to claim 2, wherein the acquiring step includes acquiring an EMG signal from the patient.

4. A method according to claim 1, further comprising a step of extracting each of the at least one second measurement signal from a corresponding normalized signal.

5. A method according to claim 4, wherein the extracting step includes low-pass filtering at least one of the at least one normalized signal.

6. A method according to claim 1, wherein the transforming step includes a step of performing a histogram transformation for the at least one of the at least one first measurement signal.

7. A method according to claim 6, wherein the performing step includes the steps of:
    forming an input array for each of the at least one of the at least one first measurement signal, each input array including a predetermined number of input elements storing input values sorted in a desired order;
    creating an output array comprising output elements storing a predetermined number of index values sorted in a desired order;
    for a signal value of each of the at least one of the at least one first measurement signal, determining the input element which corresponds to said signal value in respective input array; and
    transforming the signal value to the index value stored in the output element corresponding to the input element determined.

8. A method according to claim 7, wherein the forming step includes using values of the at least one of the at least one first measurement signal as the input values.

9. A method according to claim 8, further comprising a step of replacing the oldest input value in each input array by the current value of respective first measurement signal.

10. A method according to claim 7, wherein the forming step includes using fixed reference values as the input values.

11. A method according to claim 7, wherein the forming step includes using both fixed reference values and values of the at least one of the at least one first measurement signal as the input values.

12. A method according to claim 1, wherein the transforming step includes a step of performing a histogram transformation conforming at least one of the at least one first measurement signal to a Gaussian distribution.

13. A method according to claim 1, wherein the acquiring step includes acquiring one physiological signal representing a physiological quantity measured from the patient, whereby one normalized signal is obtained in the transforming step and one second measurement signal monitored in the monitoring step.

14. A method according to claim 13, wherein the setting step includes setting a threshold value based on said one normalized signal.

15. A method according to claim 14, wherein the setting step includes setting a threshold value proportional to the standard deviation of said one normalized signal.

16. A method according to claim 15, wherein the monitoring step includes monitoring the number of times that said one second measurement signal crosses the threshold value in a predetermined direction during a time unit.

17. A method according to claim 13, wherein the acquiring step includes acquiring said one physiological signal from among a set of signals including an RRI signal, a plethysmographic signal, an EMG signal, and a signal representing skin conductivity.

18. A method according to claim 1, wherein the acquiring step includes acquiring a plurality of physiological signals from the patient, each physiological signal representing a physiological quantity measured from the patient, whereby a plurality of normalized signals are obtained.

19. A method according to claim 18, wherein the acquiring step includes acquiring said plurality of physiological signals from among a set of signals including an RRI signal, a plethysmographic signal, an EMG signal and a signal representing skin conductivity.

20. A method according to claim 18, wherein the setting step includes setting at least one threshold surface residing in a space defined by the plurality of normalized signals.

21. A method according to claim 1, wherein the acquiring step includes acquiring at least one first measurement signal indicative of pain experienced by the patient.

22. A method according to claim 21, further comprising a step of determining the at least one first measurement signal based on a set of physiological signals obtained from the patient.

23. A method according to claim 1, wherein at least one of the at least one second measurement signal is indicative of noxious responses in the patient.

24. A method according to claim 23, wherein at least one of the at least one second measurement signal is further indicative of non-noxious responses in the patient.

25. A method according to claim 1, wherein at least one of the at least one second measurement signal is indicative of non-noxious responses in the patient.

26. A method according to claim 1, further comprising a step of determining, based on the rate monitored, an index signal for the patient, the index signal being indicative of pain experienced by the patient.

27. A method according to claim 26, wherein the determining step includes transforming the rate into a normalized signal having a predetermined value range.

28. A method according to claim 1, wherein the monitoring step includes monitoring the number of times that the at least one second measurement signal fulfills the threshold condition during a time unit.

29. A method according to claim 1, wherein the monitoring step includes monitoring the proportion of time that the threshold condition remains to be fulfilled by the at least one second measurement signal.

30. An apparatus for monitoring pain-related responses in a patient, the apparatus comprising:
   first means for acquiring at least one first measurement signal from a patient;
   transformation means for transforming at least one of the at least one first measurement signal into a normalized signal having a predetermined value range, whereby at least one normalized signal is obtained;
   second means for setting a threshold condition based on the at least one normalized signal; and
   third means for monitoring a rate at which at least one second measurement signal fulfills the threshold condition, wherein each of the at least one second measurement signal is derivable from a corresponding normalized signal and indicative of pain-related activity in the patient.

31. An apparatus according to claim 30, further comprising fourth means for extracting each of the at least one second measurement signal from a corresponding normalized signal.

32. An apparatus according to claim 31, wherein the first means are configured to receive at least one physiological signal measured from the patient, each physiological signal representing a physiological variable measured from the patient.

33. An apparatus according to claim 32, wherein the at least one physiological signal forms the at least one first measurement signal.

34. An apparatus according to claim 32, wherein the first means are further provided with first calculation means for deriving the at least one first measurement signal based on the at least one physiological signal.

35. An apparatus according to claim 31, wherein the fourth means include filtering means for filtering at least one of the at least one normalized signal.

36. An apparatus according to claim 30, wherein the transformation means are configured to perform a histogram transformation for the at least one of the at least one first measurement signal.

37. An apparatus according to claim 36, wherein the transformation means comprise:
   means for forming an input array for each of the at least one of the at least one first measurement signal, each input array including a predetermined number of input elements storing input values sorted in a desired order;
   means for creating an output array comprising output elements storing a predetermined number of index values sorted in a desired order;
   determination means for determining, for a signal value of each of the at least one of the at least one first measurement signal, the input element which corresponds to said signal value in respective input array; and
   means for transforming the signal value to the index value stored in the output element corresponding to the input element Indicated by the determination means.

38. An apparatus according to claim 37, wherein the means for forming the input array are configured to update the input values.

39. An apparatus according to claim 37, wherein the input array stores fixed reference values as the input values.

40. An apparatus according to claim 30, wherein the second means are configured to define at least one threshold value based on at least one of the at least one normalized signal.

41. An apparatus according to claim 30, further comprising second calculation means, responsive to the third means, for calculating an index signal having a predetermined value range.

42. An apparatus according to claim 41, wherein the second calculation means are provided with means for performing a histogram transformation.

43. An apparatus according to claim 41, further comprising means for supplying the index signal to a device controlling infusion of an analgetic to the patient.

* * * * *